United States Patent [19]

Hassler

[11] 4,197,750

[45] Apr. 15, 1980

[54] ULTRASONIC IMAGING APPARATUS OPERATING ACCORDING TO THE IMPULSE-ECHO METHOD

[75] Inventor: Dieter Hassler, Erlangen, Fed. Rep. of Germany

[73] Assignee: Siemens Aktiengesellschaft, Berlin & Munich, Fed. Rep. of Germany

[21] Appl. No.: 902,114

[22] Filed: May 2, 1978

[30] Foreign Application Priority Data

May 31, 1977 [DE] Fed. Rep. of Germany ....... 2724437

[51] Int. Cl.² ............................................. G01N 29/00
[52] U.S. Cl. ...................................... 73/629; 128/660; 367/46; 367/900; 367/87
[58] Field of Search .......... 128/2 V, 2.05 Z, 660–661; 73/597–600, 629–631; 364/821, 825, 827; 340/15.5 F, 1 R

[56] References Cited

U.S. PATENT DOCUMENTS

| | | | |
|---|---|---|---|
| 3,033,029 | 5/1962 | Weighart | 73/631 X |
| 3,076,177 | 1/1963 | Lawrence et al. | 340/15.5 F X |
| 3,150,327 | 9/1964 | Taylor | 364/825 |
| 3,162,756 | 12/1964 | Lawrence | 340/15.5 F X |
| 3,287,695 | 11/1966 | Taylor | 340/15.5 F X |
| 3,309,914 | 3/1967 | Weighart | 73/631 X |
| 3,805,596 | 4/1974 | Klahr | 128/2 V X |
| 4,016,750 | 4/1977 | Green | 128/2 V X |
| 4,057,049 | 11/1977 | Hill | 128/2.05 Z X |

OTHER PUBLICATIONS

Wells, P. N. T., "Electronically Controlled Attenuators," in *Physical Principles of Ultrasonic Diagnosis*, Academic Press, London & N.Y., 1969, pp. 110–116.

*Primary Examiner*—Robert W. Michell
*Assistant Examiner*—Francis J. Jaworski
*Attorney, Agent, or Firm*—Hill, Van Santen, Steadman, Chiara & Simpson

[57] ABSTRACT

The apparatus comprises an ultrasonic transducer for the purpose of scanning an examination subject, and an image display device for representation of the ultrasonic information signals in the form of a display image. In accordance with the illustrative disclosure, an arrangement of electric frequency filters is associated with the ultrasonic transducer, said frequency filters manifesting a frequency response which is essentially the inverse of the frequency response being imposed on the ultrasonic impulses by the attenuating examination subject in the ultrasonic-transmit path. The imaging apparatus finds application particularly in medical ultrasonic diagnosis.

12 Claims, 6 Drawing Figures

ULTRASONIC IMAGING APPARATUS OPERATING ACCORDING TO THE IMPULSE-ECHO METHOD

BACKGROUND OF THE INVENTION

The invention relates to an ultrasonic imaging apparatus operating according to the impulse echo method, comprising an ultrasonic transducer for scanning, particularly also for linear scanning, of an examination subject, and comprising an image display device for representation of the ultrasonic-echo signals in the form of an echo display image.

In apparatus of this type, among which are very generally included so-called compound-scanners, sector-scanners, or also rotational and array B-scanners, and/or also random A-scanners and Doppler-scanners, the quality of the ultrasonic echo images produced still leaves much to be desired. In particular, an improved transverse resolution is desirable, and echo-producing structures which are tangentially subjected to ultrasound should be better capable of representation. It is known from the physics of sonic fields that both cited properties are improved with an increasing sonic frequency. However, an increase in the frequency beyond the hitherto conventional values would lead, in the case of the known apparatus, to a reduction of the maximum possible penetration depth of the ultrasound in the area under examination.

SUMMARY OF THE INVENTION

It is the object of the invention to construct an imaging apparatus such that optimum values nevertheless result with regard to transverse resolution and the maximum possible penetration depths.

In accordance with the invention, the object is achieved by virtue of the fact that an arrangement of electric frequency filters is associated with the ultrasonic transducer which manifest a frequency response characteristic which is essentially the inverse of the frequency response imposed on the ultrasonic impulses by the attenuating examination subject in the ultrasonic transit path.

In comparison with a hitherto only possible frequency-independent transit time-dependent depth compensation amplification (e.g. German Pat. No. 2,062,177), in the case of the present invention, such a depth compensation amplification is carried out with frequency-dependency. Losses are hereby compensated or even over-compensated which the ultrasonic impulse is subject to on its path through the examination subject due to frequency-dependent subject-attenuation. However, it is thereby also possible to partially convert excessive amplitude-dynamics of the image information into improved resolution. Experiments have shown that the losses in transverse resolution which result from the frequency-dependent ultrasonic-subject attenuation can be cancelled to such an extent that an improvement by a factor of 1.2 to 2 can be achieved without having to increase the frequency of the radiated ultrasound beyond the hitherto conventional values, which, of course, as is known, would lead to a reduction in the penetration depth. However, the invention provides not only an improved transverse resolution with an optimum penetration depth; by pre-emphasizing high frequency components in the arrangement of the frequency filters, the representation of structures impinged upon tangentially is also improved because the scattering (or dispersion), as is known, increases with the frequency. The invention can be used with great advantage in the case of all ultrasonic apparatus of the type initially cited. The method of frequency-dependent transit time amplification, however, acquires yet further significance in computer-tomography with ultrasound. In the so-called transit time method, where the transit time of the ultrasound passages through an examination subject are determined for further processing, the tissue-conditioned pulse-shape distortion entails problems of precise time measurement (trigger point at the pulse edge of variable slope). However, the present invention permits a restoration of the pulse shape, wherein the attenuation, by way of example, is determined by measurement of the amplitudes and the inverse filter formation is adjusted in dependence upon the measurement result; i.e., in dependence upon the measured amplitudes. Thus, in accordance with the invention, the examination subject can be treated in the region of the ultrasonic transit path as a "tissue (frequency) filter," to which an "inverse tissue filter" is connected. However, the series-connection corresponds to the multiplication of the frequency responses; thus, a frequency-independent transmission path for ultrasonic impulses results which transmits the acoustically radiated-in ultrasonic impulses in a true to form (or shape) manner. The arrangement, forming the "inverse tissue filter," of electronic frequency filters, of course, does not affect the acoustic wave form (or shape) at the locations of reflection in the examination subject. The waveform further comprises high frequency components; however, in a weakened form. The "inverse filter" merely increases the weakened frequency components; i.e., it weights these altogether more strongly in comparison with lower frequency components. The arrangement of an "inverse tissue filter" specifically on the receiving side is not absolutely necessary; the correction filter can likewise be split (or divided) into two components. Thus, a filter component is disposed on the transmission side and distorts the transmission signal in precisely such a fashion that, subsequent to passage, it arrives at the reflection location in the examination subject in a non-distorted manner. The second filter-half is disposed on the receiving side and effects a distortion correction of the influencing of the return from the reflection location to the transmitter/receiver. Since it is a question of linear distortions, a random interchange in the sequence of the tandem members is without influence, such that it is permissible to combine both filter halves into one single arrangement of inverse frequency filters selectively on the receiving or on the transmitting end (interchange of multiplicands). In the same manner, instead of filtering all individual signals, it is necessary to effect a filtering operation only once after summation (factoring out a common factor of all addenda). However, a prerequisite for this is a restriction (or limitation) in the aperture in order to keep the transit path or attenuation differences small percentage-wise, such that the factored-out factor is also common to all addenda. By means of the latter, the method can also be applied to non-subdivided transmission/receiving vibrators. Here, the addition of all partial signals takes place by means of direct parallel connection of the transducer elements to one single large transducer.

In a first advantageous embodiment of the invention, an automatic tuning control system is to be associated with the arrangement of the frequency filters, said control system dynamically adapting (or matching) the frequency response of the filter arrangement to the respective depth position of the echo-producing structure in the examination subject when echo impulses arrive in the receiving mode from these depth positions. For purposes of adaptation (or matching), in an arrangement with preferably electronically detunable frequency filters, the fixedly prescribed inverse frequency response should be dynamically displaceable from higher to lower frequencies by way of the automatic tuning control system. A further advantageous embodiment of the invention, by way of contrast, is characterized in that, in order to effect adaptation (or matching), a plurality of individual filters, which are tuned separately and in a stepped (or graduated) fashion in frequency response sections (or segments) to varying depth-position-regions, are capable of successive interrogation in a chronologically graduated (or staggered) fashion by means of selection switches. The individual filters are here preferably connected in a tandem formation whereby, though the selection switches, beginning with a first individual switch, additional following tandemly connected filters are capable of being tapped in chronological succession pursuant to switching-off of the preceding filters. In comparison with the current frequency-independent transit time-dependent amplification degree regulation (or control) for example, in accordance with the German Pat. No. 2,062,177, the inverse filtering provides a very strong emphasis of the high frequency portions (beyond the nominal or transmitting frequency) and a de-emphasis of the low frequencies. The super-proportional emphasis (or increase) in the high frequencies affects the useful (or signal) voltages and the interference voltages equally. Since the signal-to-noise ratio of the high frequency useful signal components is less than that of the low frequency useful signal components, the signal-to-noise ratio and hence also the maximum penetration depth during application of the inverse filtering could be reduced. However, this can be readily avoided in that, in a further advantageous embodiment of the invention, the arrangement of the frequency filters for the inverse filtering manifests a frequency response which is set above a depth-dependent concomitant cut-off (or limit) frequency.

Additional advantages and details of the invention will be apparent from the following description of a sample embodiment on the basis of the accompanying sheets of drawings; other objects, features and advantages will be apparent from this detailed disclosure and from the appended claims.

DETAILED DESCRIPTION

Figure 1:
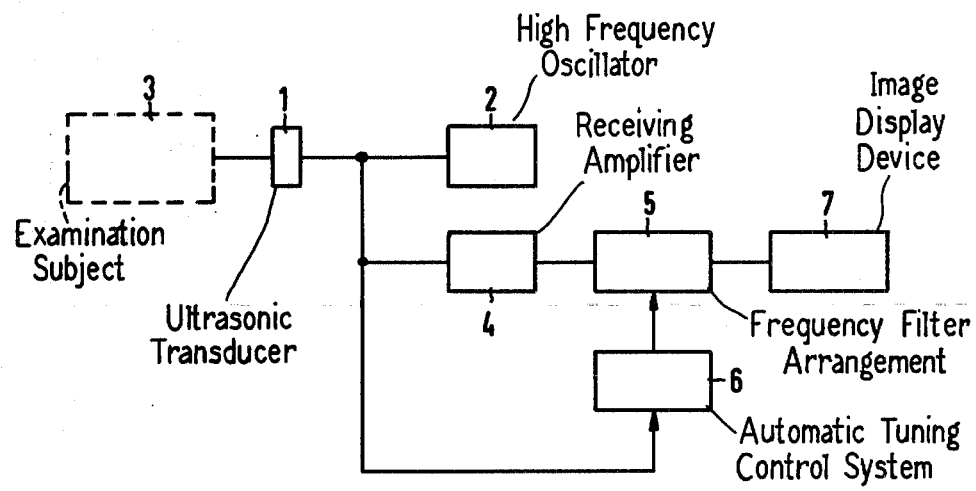
FIG. 1 illustrates a sample embodiment of the invention with an electronically detunable "inverse frequency filter" in a basic circuit diagram.
Figure 2:
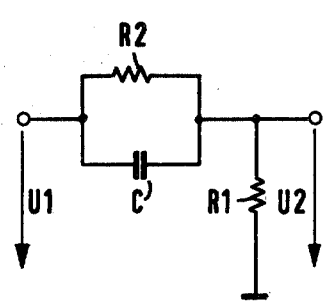
FIGS. 2 and 3 illustrate basic elements of a cascade arrangement of electronically detunable frequency filters which, altogether, determine the inverse frequency response.
Figure 3:
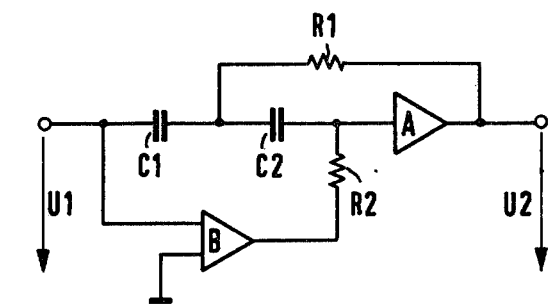

In FIG. 1, 1 designates an ultrasonic transducer (for example, a piezoceramic vibrator), which can function as a transmitter and simultaneously also as a receiver of ultrasonic signals. Ultrasonic transducer 1, which is fed by high frequency impulses of a high frequency oscillator 2, may be the transducer of a compound scanner or also of a sector scanner. It can likewise also be the rotating transducer of a rotational-scanner with a parabolic reflector. An additional possibility is that transducer 1 may be a part of an ultrasonic array comprising a plurality of corresponding transducers. Transducer 1 may also be the transmitting/receiving head of an A-scanner or of a Doppler-scanner. Ultrasonic transducer 1 of FIG. 1 radiates ultrasonic transmission impulses in the cadence of the high frequency pulses of high frequency oscillator 2 into body tissue of a examination subject 3 illustrated in broken lines. The echo signals originating from various depth regions of the examination subject 3 are again received (or picked up) by transducer 1 and conveyed to a receiving amplifier 4. Via an arrangement 5 of frequency filters with an automatic tuning control system 6, they reach an image display device 7 (electron beam tube). The frequency response of arrangement 5 of frequency filters is essentially the inverse of the frequency response exerted on the ultrasonic impulses of transducer 1 by the attenuating examination subject 3 in the ultrasonic transit path. Thus, if examination subject 3 forms the tissue filter, the arrangement 5 of the frequency filters forms the "inverse tissue filter." As examinations have shown, the frequency response of the tissue filter can be approximated in the simplest fashion by a series-connection of Butterworth-filters of increasing pole-numbers and cut-off (or limit) frequencies. The "inverse tissue filter" 5 is then a corresponding tandem circuit whereby, however, poles and zero positions are interchanged as compared with poles and zero positions in the frequency response of the "tissue filter" at 3. A quite adequate electric tissue-filter phantom of the "tissue filter" is the tandem connection of a plurality of low pass circuits with, by way of example, a total of six attenuation poles and correspondingly increasing attenuation numbers for varying tissue depths; for example, the depths 5, 10, 15, and 20 cm. The simplest type of interchanging of poles and zero positions results in utilizing operational amplifiers with RC-, RL-, or RLC-members in a feedback circuit. With operational amplifiers constructed in this manner, a real zero position or also two complex zero positions can be realized. Filters with three and more zero positions can then be formed from a series connection of filters of the type described with one and two zero positions. A variation in the lower limit (or cut-off) frequency of such a filter formation through the output signals of the automatic tuning control system 6 proceeds essentially by varying the inductance L or the capacitance C, or on the basis of simultaneous variation of both values. However, the cited filters are problematic regarding stability against self-oscillations. This results from the impossibility of realizing operational amplifiers manifesting a low inherent (of self-) phase rotation up to frequencies of 10 to 20 MHz. For reasons of stability, however, this is a requirement which need be made, since in the case of practical values, the feedback network already rotates up to 150° in the phase. However, with a 180° phase rotation, the oscillation requirement is already fulfilled. However, a phase-edge (or border) of at least 30° should remain in order to avoid undesirable resonances. Individual members for the filter formation of the inverse filter 5, which guarantee a more favorable realization, are illustrated in FIGS. 2 and 3. If a band-restriction (or limitation) to high frequencies is added, purely passive elements suffice for the formation of the frequency filters. In the case of simple real pole- or zero-positions, respectively, the network of FIG. 2 satisfies the condition (or requirement):

$$\frac{U_2}{U_1} = \frac{R_1}{R_2} \cdot \frac{1 + j\frac{\omega}{\omega u}}{1 + \frac{R_1}{R_2} + \frac{\omega}{\omega o}}$$

whereby $$\omega_u = 1/R_2 C \text{ and } \omega_o = 1/R_1 C$$

A parallel displacement of the frequency response curve in the region of the lower limit (or cut-off) frequency $\omega_u$ and the upper cut-off frequency $\omega_o$ ($\omega u/\omega o = $ const) is provided in a simple fashion by means of variation of capacitance C. The variation of capacitance C can, for example, be readily effected by using capacitance diodes.

A complex pole-, zero-position pair is provided by the variation (or modification) of an active two-pole high pass filter in accordance with FIG. 3 as follows:

$$\frac{U_2}{U_1} = \underbrace{(1 - \frac{\omega u}{\omega o} + (\frac{\omega u}{\omega o})^2)}_{<<1} \cdot \frac{1 - (\frac{\omega}{\omega u})^2 + j\sqrt{2}(\frac{\omega}{\omega u})}{1 - (\frac{\omega}{\omega o})^2 + j\sqrt{2}(\frac{\omega}{\omega o})}$$

whereby $$C_1 = C_2 = C; R_1 = \frac{1}{\sqrt{2} \ \omega_u C}; \frac{R_2}{R_1} = 2B$$

$$\omega_o{}^2 = \frac{1}{R_1 R_2 C^2}; R_2 = R_1 \cdot 2B$$

$$\omega_u{}^2 = B \cdot \omega_o{}^2; A = (\frac{\omega o}{\omega u})^2 - \frac{\omega o}{\omega u} + 1; (\frac{\omega o}{\omega u})^2 = \frac{1}{B}$$

The parallel displacement of the frequency response curve is accomplished by variation in the two capacitances $C_1$ and $C_2$.

A three-pole filter, as already indicated, can be formed by the series connection of a unipolar filter with a dual-pole filter. However, to this end, the location of the pole and zero positions of the dual pole component must be displaced. From the transmission function $$\frac{U_2}{U_1} = $$

$$A \cdot B \frac{1 - \frac{\omega^2 R_1 R_2 C_1 C_2}{B} + j\omega R_1 (C_1 + C_2)}{1 - \omega^2 R_1 R_2 C_1 C_2 + j\omega(R_2 C_2 (1 - A) + R_1 (C_1 + C_2))}$$

are found the conditions $$j\omega R_1 (C_1 + C_2) = 1 \text{ at } \omega = \omega_u$$

$$j\omega(R_2 C_2 (1-A) + R_1 (C_1 + C_2)) = 1 \text{ at } \omega = \omega_o$$

whereby $$R_1 = 1/(2\omega_u C)$$

$$R_2 = 4B \ R_1$$

$$A = 1 + \frac{1}{2}(\frac{\omega o}{\omega u})^2 - \frac{1}{2} \frac{\omega o}{\omega u} \approx \frac{1}{2}(\frac{\omega o}{\omega u})^2$$

Figure 4:
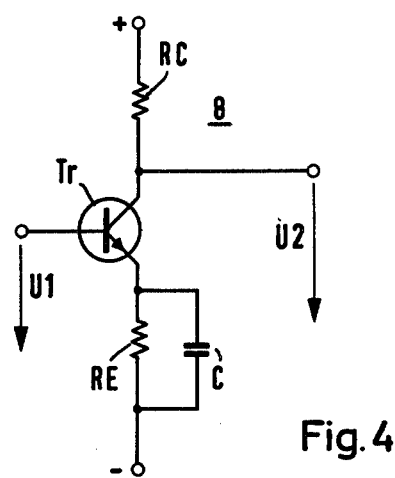
FIG. 4 illustrates a basic element of an inverse-filter cascade arrangement whose individual filters, separately and stepped (or graduated) in frequency response sections (or segments), are tuned to varying depth position regions.

The sample embodiments of FIGS. 1 through 3 describe filters with electronically tunable components for the purpose of varying the cut-off (or limit) frequency. An additional solution method is that in which operation is carried out with non-variable (fixed) components in the filters, and wherein the variation of the frequency response is carried out in a digital fashion with analog switches. A basic member for realizing this further possible solution is illustrated in FIG. 4. The RC-low pass functions are converted by one transistor $T_r$ functioning as the active decoupling member into differentiating frequency responses. Assuming that $1/s << R_E$ (where $R_E$ is the emitter resistance and s the slope of the transistor), the transmission function results as follows:

$$\frac{U_2}{U_1} = R_C(\frac{1}{R_E} + j\omega C) =$$

$$\frac{R_C}{R_E}(1 + j\omega R_E C) = v_o (1 + j\frac{\omega}{\omega_o})$$

with $$v_o = R_C/R_E \text{ and } \omega_o = 1/(R_E C)$$

Figure 5:
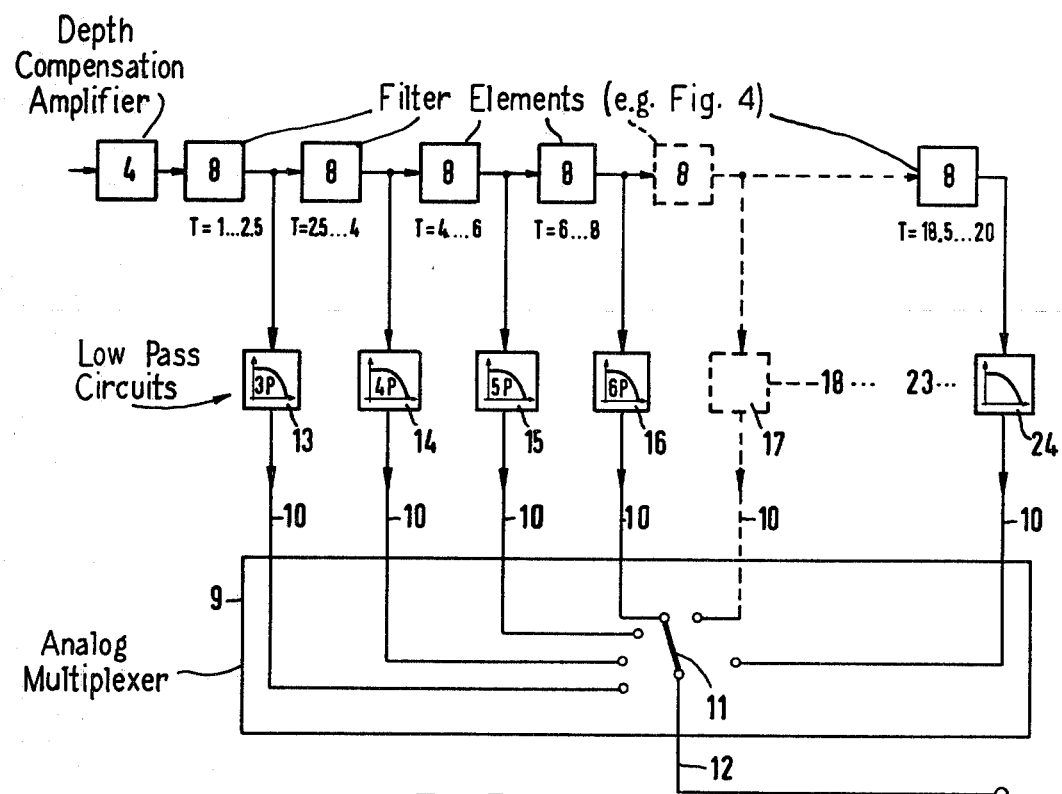
FIG. 5 illustrates a first sample embodiment of an inverse filter tandem arrangement in a basic circuit diagram based on fundamental elements in accordance with FIG. 4 and low-pass circuits in a fixed element construction.
Figure 6:
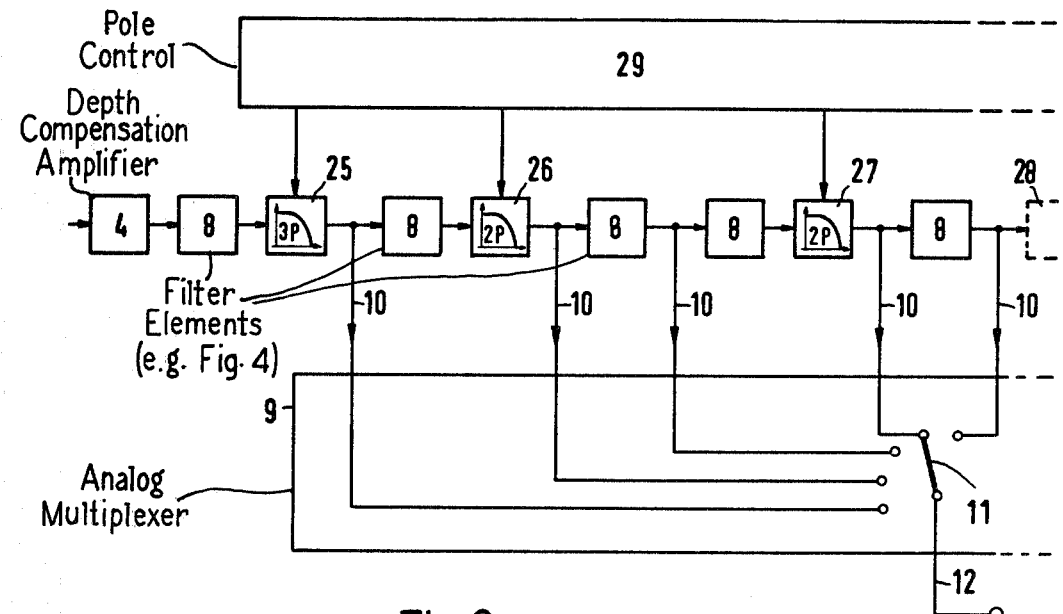
FIG. 6 illustrates a second sample embodiment of an inverse filter tandem arrangement in a basic circuit diagram based on fundamental elements according to FIG. 4 which, however, does not function with fixed, but with variable, low-pass circuits.

According to FIGS. 5 and 6, preferably twelve such transistor circuits are connected in series as tandem filter elements 8. The amplification factors $v_o$ are selected such that all stages at 2.00 MHz exhibit an amplification of one (unity gain). Too rough a graduation of the amplification factors is thereby avoided. The series connection with a conventional depth compensation amplifier 4 results in a stepless (or non-graduated) amplification adaptation. The receiving signal is tapped (or picked off) in a depth-dependent fashion only at the location of the tandem circuit which manifests the suitable slope (or steepness) of the frequency response curve. The step-width of the slope graduation is selected to be sufficiently fine. The selection proceeds via an analog multiplexer 9 with tap lines 10, electronic switch 11, and output line 12. A significant element in the realization consists in the variable upper cut-off frequency, above which the frequency response rise changes to a drop (or decrease). FIGS. 5 and 6 illustrate two solution possibilities. In the sample embodiment of FIG. 5, LC low pass filters 13 through 24 with varying cut-off frequencies $\omega_{e1}$ through $\omega_{e12}$ and pole numbers 3P, 4P ... 14P are placed in the branch lines between transistor circuits 8 and tap lines 10 of the multiplexer 9. The number of poles is to be at least greater by two than the sum of the zero positions in the preceding differentiating tandem members 8. In addition, the poles are disposed such that a maximum flat amplitude frequency response results. The cut-off frequencies are positioned (or set) such that the minimum justifiable dynamic range is adhered to. The depth regions T (in cm), illustrated in the block circuit diagram of FIG. 5, apply to the instance of compensation without differentiation. The cut-off frequencies of the low pass filters 13 through 24, for 5, 10, 15 and 20 cm penetration depths, amount preferably to 3.46 MHz, 3.00 MHz, 2.00 MHz and 1.42 MHz. The cited values apply to immediate representation of the ultrasonic images. If operation is carried out with image storage wherein the image is subdivided into a sufficiently large number of image lines, and the information of a plurality of images (for example, 100 images) is added separately for each individual images line in an image memory, an increased signal to noise ratio results which permits higher cut-off frequencies of the low pass filters at the same depth. Regarding the above-selected depth ranges of 5, 10, 15, and 20 cm penetration depth, there thus results increased cut-off frequencies of 3.60; 3.28; 2.8 and 2.00 MHz with an unchanged transmission frequency of approximately 2.00 MHz. In case of differentiation, the first seven low-pass filters are not required. Echoes from skin-proximate structures are then tapped (or picked off) behind the eighth differentiating element. Beginning already with a 15 cm depth position of the echo producing structures, the receiving signals are tapped behind the last differentiating member and transported through low pass filters of varying cut-off frequencies (for example, a fourteen-pole low pass filter with 2.00 MHz limit frequency at a 15 cm depth position and 1.4 MHz at a 20 cm depth position). The realization form of FIG. 5 operates with fixed components which, particularly in view of the multi-pole low-pass filters leads to a non-inconsiderable circuit outlay. However, the sample embodiment of FIG. 6 avoids an excessive outlay, said sample embodiment, however, requiring electronically detunable capacitances and inductances. In contrast with the sample embodiment of FIG. 5, eight LC-low-pass filters 25, 26, 27, 28, etc., are now connected between the differentiating filter stages 8. With a progressive tap 10, there results, in connection with a pole control 29 (for example, a microprocessor) the successive switching-over from a three-pole Butterworth in the first position to a five-pole Butterworth-filter in the second position, as well as corresponding higher-pole Butterworth-filters for the next-higher taps (or tapping locations). Due to the displacement of the pole-positions via the pole control 29, the cut-off frequency is also displaced for every new multi-pole Butterworth filter. Electronically variable coils and capacitors are roughly variable in the ratio of 1:4. In this ratio, the limit frequency can thus be displaced without variation in the resistance level. Since the actual limit frequency displacement, in any case, proceeds with a factor of 3.5 MHz/1.4 MHz=2.5, there are no realization problems in this regard.

It will be apparent that many modifications and variations may be effected without departing from the scope of the novel concepts and teachings of the present invention.

I claim as my invention:

1. An ultrasonic imaging apparatus functioning according to the impulse echo method, with an ultrasonic transducer (1) for scanning an examination subject (3), particularly, also a linewise scanning, and an image display device (7) for the representation of the ultrasonic echo signals as a visible echo image, an arrangement (5) of frequency filters being allocated to the ultrasonic transducer (1), which frequency filters exhibit a frequency response which is essentially inverse to that frequency response which is exerted by the attenuating examination subject on the ultrasonic pulses in the ultrasonic transmit path, and an automatic tuning control system (6) being allocated to said arrangement (5) by means of which the prescribed inverse frequency response is dynamically shiftable from higher to lower frequencies to that degree to which echo pulses occur from increasingly deeper layers of the examination subject (3), wherein the improvement comprises, said filter arrangement (5) having a common filter input, having a multitude of individual filter circuits (8, 13 through 24 or 8, 25 through 28) coupled with said common filter input, said individual filter circuits having respective frequency response characteristics for adapting to different depth positions within the examination subject (3), said individual filter circuits having respective individual filter outputs for supplying respective output signals adapted in their respective frequency response characteristics to respective different depth positions; having selection switch means (11) coupled with each of said individual filter circuits at the respective individual filter outputs thereof, said selection switch means (11) being controlled by said automatic tuning control system (6) in synchronization with the occurrence of ultrasonic information signals from increasing depth positions within the examination subject, to successively connect the respective individual filter outputs of the respective individual filter circuits in a temporal sequence, and means connected with the selection switch means for supplying said respective output signals in a sequential manner to the image registering device (7).

2. An ultrasonic imaging apparatus according to claim 1, characterized in said individual filter circuits being coupled in a tandem formation, said selection switch means being operable to tap the individual filter circuits of the tandem formation beginning at the individual filter output of a first one of said filter circuits and then at the individual filter outputs of additional following ones of said filter circuits in chronological succession.

3. An ultrasonic imaging apparatus according to claim 2, with means (4) providing a frequency-independent amplitude-depth compensation, said individual filter circuits in the case of a specified nominal frequency being such that the amplitude transmission factor between all individual filter outputs (10) and the common filter input is of equal magnitude, and only the slope of the frequency response provided by the respective filter circuits at said nominal frequency is variable according to the position of the filter circuits in said tandem formation.

4. An ultrasonic imaging apparatus according to claim 1, characterized in that the arrangement (5) exhibits a frequency response which is cut off above a depth-dependent cut-off frequency.

5. An ultrasonic imaging apparatus according to claim 1, wherein the individual filter circuits comprise Butterworth filters, said arrangement (5) providing a tandem circuit coupling said Butterworth filters.

6. An ultrasonic imaging apparatus according to claim 1, wherein the arrangement (5) of the frequency filters comprises a tandem coupling of said filter circuits, said filter circuits comprising differentiating RC filter elements each comprising a resistance-capacitance circuit (8) and a form member (Tr), with the form member converting the pole/zero positions of the filter circuit to zero/pole positions of the transmission function.

7. An ultrasonic imaging apparatus according to claim 6, wherein each form member comprises a transistor (Tr) having an emitter circuit, and wherein each RC filter element comprises resistance and capacitance means in the emitter circuit of one of said transistors (Tr).

8. An ultrasonic imaging apparatus according to claim 6, wherein said individual filter circuits further comprise low pass circuits in said tandem coupling, said low pass circuits (13 through 24) having fixedly preselected pole-positions and cut-off frequencies for different subject-depths.

9. An ultrasonic imaging apparatus according to claim 8, wherein said low pass circuits have increasing numbers of poles along the tandem coupling.

10. An ultrasonic imaging apparatus according to claim 6 wherein said individual filter circuits further comprise low pass circuits (25 through 28),
said automatic tuning control system comprising a pole control (29) coupled with said low pass circuits for varying the pole positions therein and hence the cut-off frequencies.

11. An ultrasonic imaging apparatus according to claim 10, wherein said differentiating RC filter elements (8) and said low pass circuits (25 through 28) are in series in said tandem coupling of said filter circuits.

12. An ultrasonic imaging apparatus according to claim 1, wherein said selection switch means comprises analog-time multiplex means (11).

* * * * *